(12) United States Patent
Sachdev et al.

(10) Patent No.: US 10,327,711 B2
(45) Date of Patent: Jun. 25, 2019

(54) POST-HOSPITAL-DISCHARGE COPD-PATIENT MONITORING USING A DYNAMIC BASELINE OF SYMPTOMS/MEASUREMENT

(71) Applicant: KONINKLIJKE PHILIPS N.V., Eindhoven (NL)

(72) Inventors: Birpal Singh Sachdev, Delmont, PA (US); Robert William Murdoch, Kennesaw, GA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 335 days.

(21) Appl. No.: 14/776,032

(22) PCT Filed: Mar. 5, 2014

(86) PCT No.: PCT/IB2014/059468
§ 371 (c)(1),
(2) Date: Sep. 14, 2015

(87) PCT Pub. No.: WO2014/147507
PCT Pub. Date: Sep. 25, 2014

(65) Prior Publication Data
US 2016/0029971 A1 Feb. 4, 2016

Related U.S. Application Data

(60) Provisional application No. 61/802,883, filed on Mar. 18, 2013.

(51) Int. Cl.
*A61B 5/08* (2006.01)
*A61B 5/00* (2006.01)
(Continued)

(52) U.S. Cl.
CPC .............. *A61B 5/7271* (2013.01); *A61B 5/08* (2013.01); *A61B 5/746* (2013.01); *G06F 19/3418* (2013.01); *G16H 50/70* (2018.01)

(58) Field of Classification Search
CPC ......... A61B 5/7271; A61B 5/746; A61B 5/08; G06F 19/3418; G06F 19/3443
See application file for complete search history.

(56) References Cited

U.S. PATENT DOCUMENTS

2001/0020229 A1* 9/2001 Lash ....................... B82Y 10/00
705/3
2004/0172080 A1* 9/2004 Stadler ................ A61B 5/0537
607/17
(Continued)

FOREIGN PATENT DOCUMENTS

JP 2009532072 A 9/2009
JP 2012532668 A 12/2012

OTHER PUBLICATIONS

Bischoff et al, "Validity and Utility of a New Tool to Measure Exacerbation Rates in Prospective Clinical COPD Studies", Dept. of Primary and Community Care, Undated, p. 1-30.
(Continued)

*Primary Examiner* — Navin Natnithithadha
*Assistant Examiner* — Andrey Shostak
(74) *Attorney, Agent, or Firm* — Michael W. Haas

(57) ABSTRACT

Systems and methods for monitoring subjects after discharge from a hospital use a dynamic baseline to determine whether a caregiver needs to be notified regarding exacerbation of a medical state of a subject. The subjects are chronic obstructive pulmonary disease (COPD) patients. The dynamic baseline is determined by aggregating (for example averaging) multiple values of a sequence of values for a metric that quantifies one or both of a patient symptom (e.g. the number of overnight apnea occurrences) and/or
(Continued)

lung function of a subject (e.g. forced expiratory volume in 1 second). Multiple metrics may be combined to generate the value that is monitored for a subject.

20 Claims, 7 Drawing Sheets

(51) Int. Cl.
  *G06F 19/00* (2018.01)
  *G16H 50/70* (2018.01)

(56) References Cited

U.S. PATENT DOCUMENTS

| | | | | |
|---|---|---|---|---|
| 2006/0253045 | A1* | 11/2006 | Coifman | A61B 5/0871 600/538 |
| 2006/0271410 | A1* | 11/2006 | Rosenfeld | G08B 25/08 705/3 |
| 2008/0270080 | A1* | 10/2008 | Zong | A61B 5/00 702/188 |
| 2008/0294060 | A1 | 11/2008 | Haro | |
| 2009/0088606 | A1* | 4/2009 | Cuddihy | A61B 5/0002 600/300 |
| 2011/0009753 | A1 | 1/2011 | Zhang | |
| 2011/0009760 | A1 | 1/2011 | Zhang | |
| 2011/0201901 | A1* | 8/2011 | Khanuja | A61B 5/00 600/300 |
| 2012/0130198 | A1* | 5/2012 | Beaule | G06F 19/3431 600/300 |
| 2013/0082837 | A1* | 4/2013 | Cosentino | G06F 19/3418 340/539.12 |
| 2013/0245502 | A1 | 9/2013 | Lange | |
| 2015/0186602 | A1* | 7/2015 | Pipke | A61B 5/743 705/3 |

OTHER PUBLICATIONS

Basilakis et al, "Design of a Decision-Support Architecture for Management of Remotely Monitored Patients", XP011327753, IEEE Transactions on Information Technology in Biomedicine, vol. 14, No. 5, 2010, pp. 1216-1226.
Bhowmik et al, "Relation of Sputum Inflammatory Markers to Symptoms and Lung Function Changes in COPD Exacerbations", Thorax, vol. 55, 2000, pp. 114-120.
Colantonio et al, "A Decision Making Approach for the Remote, Personalized Evaluation of COPD Patients' Health Status", Proceedings of the 7th International Workshop on Biosignal Interpretation, 2012, pp. 347-350.
Papaioannou et al, "Global Assessment of the COPD Patient: Time to Look Beyond FEV1?", Respiratory Medicine, vol. 103, 2009, pp. 650-660.
Criner, MD, "Telemedicine to Prevent COPD Exacerbtions", School of Medicine, Temple University, 2010, 2 Pages.
Seemungal et al, "Time Course and Recovery of Exacerbations in Patients With Chronic Obstructive Pulmonary Disease", American Journal of Critical Care Medicine, vol. 161, 2000, pp. 1608-1613.
Vitacca et al, "Tele-Assistance in Chronic Respiratory Failure Patients: A Randomised Clinical Trial", European Respiratory Journal, vol. 33, 2009, pp. 411-418.
Vijayasaratha, "Reported and Unreported Exacerbations of COPD*", Chest Journal, vol. 133, 2008, pp. 34-41.

* cited by examiner

POST-HOSPITAL-DISCHARGE COPD-PATIENT MONITORING USING A DYNAMIC BASELINE OF SYMPTOMS/MEASUREMENT

CROSS-REFERENCE TO PRIOR APPLICATIONS

This application is the U.S. National Phase application under 35 U.S.C. § 371 of International Application No. PCT/IB2014/059468, filed on Mar. 5, 2014, which claims the benefit of U.S. Provisional Patent Application No. 61/802,883, filed on Mar. 18, 2013. These applications are hereby incorporated by reference herein.

BACKGROUND

1. Field

The present disclosure pertains to systems and methods for monitoring subjects after discharge from a hospital, and, in particular, to monitoring chronic obstructive pulmonary disease (COPD) patients using a dynamic baseline that quantifies symptoms and/or measurements to determine whether medical intervention is warranted.

2. Description of the Related Art

Chronic obstructive pulmonary disease (COPD) affects many patients. Patient monitoring or tracking, during a hospital stay and/or at home, may be useful for different types of patients. Information gathered during patient monitoring may be indicative of a need to intervene medically. For example, certain symptoms for certain patients may indicate a worsened (or worsening of a) condition of a patient. False positive indications of a need to intervene may be costly and/or otherwise undesirable, e.g. for medical and/or policy reasons.

SUMMARY

Accordingly, one or more embodiments provide a system configured to monitor subjects. The subjects are chronic obstructive pulmonary disease patients. The system comprises one or more processors configured to execute computer program modules. The computer program modules comprise a metric module, a dynamic baseline module, and an alert module. The metric module is configured to obtain a sequence of values for a first metric that quantifies one or both of a patient symptom and/or lung function of a subject. Individual values correspond to different times, such that individual values in the sequence correspond to times during a defined period. The dynamic baseline module is configured to determine dynamic baselines for subjects, such that a first dynamic baseline is determined for the subject by aggregating multiple individual values of the sequence. The alert module is configured to determine whether a caregiver and/or a clinician needs to be notified regarding exacerbation of a medical state of the subject. The determination by the alert module is based on a comparison of one or more individual values for the first metric from the metric module and the first dynamic baseline.

It is yet another aspect of one or more embodiments to provide a method for monitoring subjects. The subjects are chronic obstructive pulmonary disease (COPD) patients. The method comprises obtaining a sequence of values for a first metric that quantifies one or both of a patient symptom and/or lung function of a subject, wherein individual values correspond to different times, such that individual values in the sequence correspond to times during a defined period; determining a first dynamic baseline for the subject by aggregating multiple individual values of the sequence; and determining whether a caregiver and/or a clinician needs to be notified regarding exacerbation of a medical state of the subject, wherein the determination is based on a comparison of one or more individual values for the first metric from the sequence and the first dynamic baseline.

It is yet another aspect of one or more embodiments to provide a system configured to monitor subjects. The subjects are chronic obstructive pulmonary disease patients. The system comprises means for obtaining a sequence of values for a first metric that quantifies one or both of a patient symptom and/or lung function of a subject, wherein individual values correspond to different times, such that individual values in the sequence correspond to times during a defined period; means for determining a first dynamic baseline for the subject by aggregating multiple individual values of the sequence; and means for determining whether a caregiver and/or a clinician needs to be notified regarding exacerbation of a medical state of the subject, wherein the determination is based on a comparison of one or more individual values for the first metric from the sequence and the first dynamic baseline.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
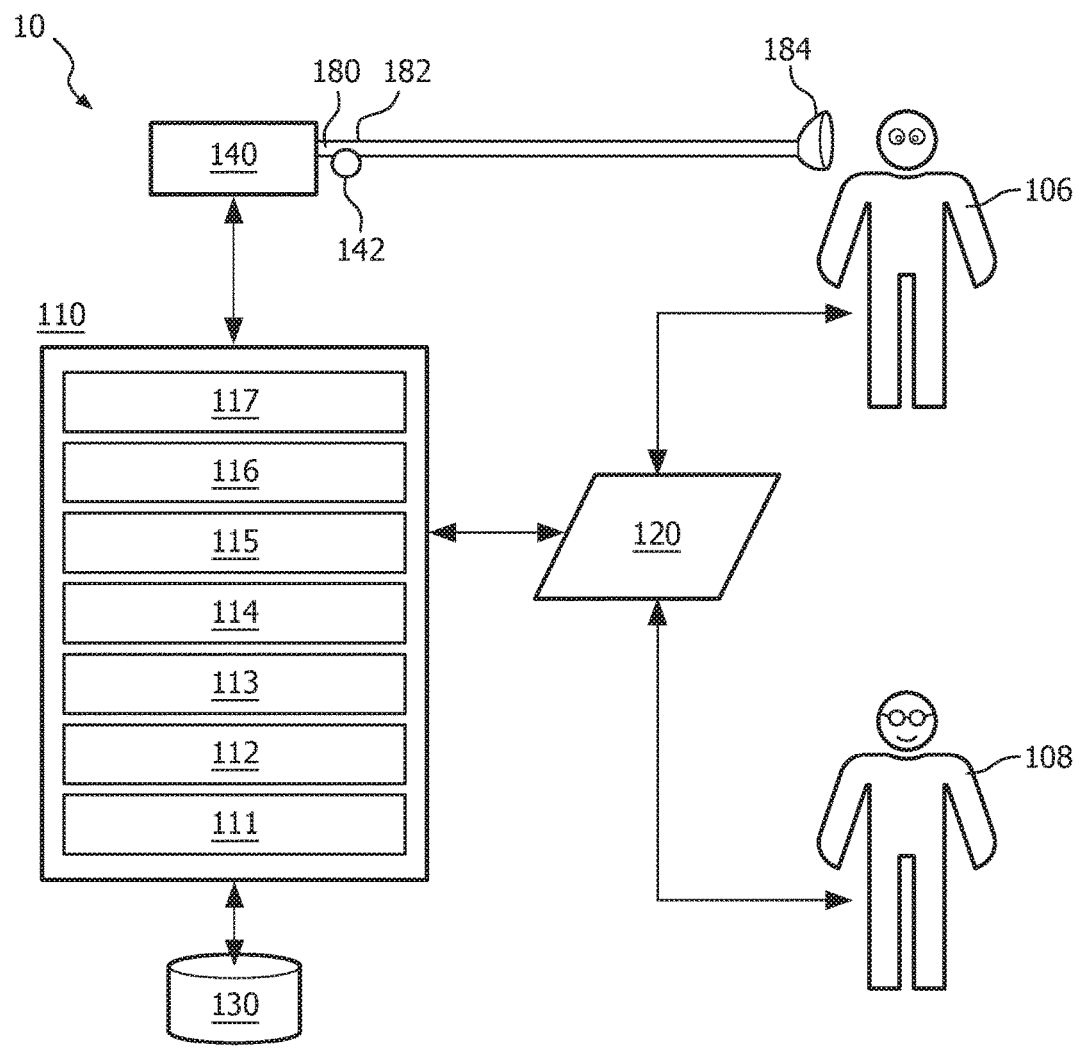
FIG. 1 schematically illustrates a system configured to monitor subjects in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 to monitor subjects. The subjects may include post hospital-discharge subjects, for example a subject 106. In some implementations, subjects may use system 10 after they have been discharged from the hospital, for example at home. The subjects may include chronic obstructive pulmonary disease (COPD) patients. System 10 includes one or more of a pressure generator 140, a delivery circuit 180, a subject interface appliance 184, one or more processors 110, one or more sensors 142, a metric module 111, a dynamic baseline module 112, an alert module 113, a variability module 114, a static baseline module 115, a long-term metric module 116, a parameter determination module 117, an electronic storage 130, a user interface 120, and/or other components and/or computer program modules. In some embodiments, system 10 may include and/or cooperate with pressure generator 140 to treat, at least, COPD and/or symptoms related thereto, and/or to measure patient symptoms related to and/or of interest in relation to a patient's COPD-status and/or lung function of a subject. In some implementations, system 10 may not need to include or cooperate with a pressure generator. For example, a subject may gather information needed as described below in other ways, including but not limited to self-reporting.

Many COPD patients are closely monitored after being discharged from the hospital (for COPD-related treatment) in order to determine whether a caregiver and/or a clinician needs to be notified. As used herein, the term "caregiver" may be interpreted to mean "caregiver and/or clinician." Notification may be advisable under certain conditions, including but not limited to exacerbation of the medical state of a subject, exacerbation of one or more COPD-related symptoms, deterioration and/or poor functioning of one or more lung functions of a subject, and/or other conditions, which may be quantifiable and/or well-defined prior to discharge from a hospital. Notifications may, under certain circumstances, lead to re-hospitalization of a subject. As used herein, the terms "monitoring" and "tracking" may be used interchangeably.

Pressure generator 140 of system 10 in FIG. 1 may be integrated, combined, or connected with a ventilator and/or (positive) airway pressure device (PAP/CPAP/BiPAP®/etc.) and configured to provide a pressurized flow of breathable gas for delivery to the airway of subject 106, e.g. via one or more subject interfaces 180. Subject interface 180 may sometimes be referred to as a delivery circuit.

Pressure generator 140 may fluidly communicate, via subject interface 180, with the airway of subject 106. Respiratory therapy may be implemented as pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Other schemes for providing respiratory support and/or ventilation through the delivery of the pressurized flow of breathable gas are contemplated. Subject 106 may but need not initiate one or more phases of respiration. The configuration of various components in FIG. 1 is not intended to limit the scope of the described technology in any way.

System 10 may be configured to adjust and/or maintain levels of pressure, flow, humidity, velocity, acceleration, and/or other parameters of the humidified, pressurized flow of breathable gas. One or more adjustments may occur in substantial synchronization with the breathing cycle of the subject. In some embodiments, one or more operating levels (e.g. pressure, volume, etc.) are adjusted on a relatively ongoing manner (e.g., each breath, every few breaths, every few seconds, etc.) during an individual session of respiratory therapy to titrate the therapy. Alternatively, and/or simultaneously, adjustments to one or more operating levels of system 10 and/or any component thereof may be made more intermittently and/or between therapy sessions rather than during a particular therapy session.

A pressurized flow of breathable gas may be delivered from pressure generator 140 to the airway of subject 106 via one or more subject interfaces 180. Subject interface 180 may include a conduit 182 and/or a subject interface appliance 184. Conduit 182 may include a flexible length of hose, or other conduit. As depicted in FIG. 1, conduit 182 may place subject interface appliance 184 in fluid communication with pressure generator 140. Subject interface 180 may include a proximal end disposed at or near humidifier 150 and a distal end disposed at or near subject interface appliance 184. Conduit 182 may form a flow path through which the pressurized flow of breathable gas is communicated between subject interface appliance 184 and pressure generator 140.

Subject interface appliance 184 of system 10 in FIG. 1 is configured to deliver the pressurized flow of breathable gas to subject 106, e.g. to the airway of subject 106. Subject interface appliance 184 may be configured to reduce and/or inhibit condensation from forming along the path of delivery of a (humidified and/or pressurized) flow of breathable gas to subject 106. Subject interface appliance 184 may include an interface body and/or other components.

In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

One or more sensors 142 of system 10 in FIG. 1 may be configured to generate output signals conveying information related to one or more parameters associated with subject 106 and/or the pressurized flow of breathable gas delivered to subject 106. The parameters may include parameters related to movement, location, position, tilt, and/or angle of subject 106 and/or a body part of subject 106, respiratory parameters, parameters of the pressurized flow of breathable gas, patient symptoms, lung function, and/or other parameters.

The one or more sensors 142 may include an accelerometer, positional sensor, movement sensor, light sensor, infrared (IR) sensor, electromagnetic sensor, electrode, tilt meter, (video) camera, body temperature sensor, thermometer, humidity sensor, smoke sensor, fine particle/airborne allergens sensor (e.g. to check pollution), and/or other sensors. The illustration of sensor 142 including one member in FIG. 1 is not intended to be limiting. In some embodiments, system 10 may use two or more sensors 142. The illustration of the location of sensor 142 as depicted in FIG. 1 is not intended to be limiting. An individual sensor 142 may be located at or near (a body part of) subject 106, embedded and/or integrated in a pillow, bed, and/or blanket, and/or at other locations. Resulting signals or information from one or more sensors 142 may be transmitted to processor 110, user interface 120, electronic storage 130, and/or other components of system 10. This transmission may be wired and/or wireless.

In some embodiments, sensor 142 may include one or more electrodes used to both provide a stimulus (e.g. in the form of an electrical pulse) and (subsequently) to sense/measure the reaction and/or response of subject 106 to that stimulus.

The one or more sensors 142 may be configured to generate output signals in an ongoing manner, e.g. before, during, and/or after a period of sleep. This may include generating signals intermittently, periodically (e.g. at a sampling rate), continuously, continually, at varying intervals, and/or in other ways that are ongoing during at least a portion of period of sleep. The sampling rate may be about 0.001 second, 0.01 second, 0.1 second, 1 second, about 10 seconds, about 1 minute, and/or other sampling rates. It is noted that multiple individual sensors 142 may operate using different sampling rates, as appropriate for the particular output signals and/or (frequencies related to particular) parameters derived therefrom. For example, in some embodiments, the generated output signals may be considered as a vector of output signals, such that a vector includes multiple samples of information conveyed as described. Different parameters may be related to different vectors. A particular parameter determined in an ongoing manner from a vector of output signals may be considered as a vector of that particular parameter.

Referring to FIG. 1, electronic storage 130 of system 10 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store sequences and/or vectors of parameters based on the generated output signals, and/or other parameters (as discussed elsewhere herein), and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., a user 108, subject 106, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed by user 108 to system 10 is patient-specific or subject-specific information related to a factor that is to be applied in determining the intensity of stimuli, such as the loudness of auditory stimuli. An example of information that may be conveyed to user 108 is an alert that a caregiver needs to be notified regarding exacerbation of the medical state of subject 106. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Processor 110 of system 10 in FIG. 1 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of metric module 111, dynamic baseline module 112, alert module 113, variability module 114, static baseline module 115, long-term metric module 116, parameter determination module 117, and/or other modules. Processor 110 may be configured to execute modules 111-117 by software; hardware; firmware; some combination of software, hardware, and/or firmware; and/or other mechanisms for configuring processing capabilities on processor 110.

It should be appreciated that although modules 111-117 are illustrated in FIG. 1 as being co-located within a single processing unit, in embodiments in which processor 110 includes multiple processing units, one or more of modules 111-117 may be located remotely from the other modules.

The description of the functionality provided by the different modules 111-117 described herein is for illustrative purposes, and is not intended to be limiting, as any of modules 111-117 may provide more or less functionality than is described. For example, one or more of modules 111-117 may be eliminated, and some or all of its functionality may be incorporated, shared, integrated into, and/or otherwise provided by other ones of modules 111-117. Note that processor 110 may be configured to execute one or more additional modules that may perform some or all of the functionality attributed below to one of modules 111-117.

Parameter determination module 117 may be configured to determine one or more parameters from output signals generated by sensor(s) 142. Determined parameters may include parameters related to COPD symptoms, COPD-status, lung function, respiratory parameters, breathing parameters, physiological parameters, gas parameters related to the (delivered) pressurized flow of breathable gas, and/or other parameters. For example, gas parameters may include and/or be related to one or more of (peak) flow, flow rate, (tidal) volume, pressure, temperature, humidity, velocity, acceleration, gas composition (e.g. concentration(s) of one or more constituents such as, e.g., water vapor or $CO_2$), thermal energy dissipated, and/or other measurements related to the pressurized flow of breathable gas or the conditions within subject interface appliance 184. For example, one or more of these gas parameters, such as pressure and/or volume, may be used during respiratory therapy.

Breathing parameters may be derived, e.g. by parameter determination module 117, from gas parameters and/or from sensor-generated output signals conveying measurements of, e.g., the pressurized flow of breathable gas. Breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters.

Operation of parameter determination module 117 may be performed in an ongoing manner, for example at a particular sampling rate. The one or more parameters may be determined at different locations and/or positions within system 10 or near subject 106. In some embodiments, parameter determination module 117 may derive vectors of parameters in an ongoing manner during a period of monitoring subject 106. The vectors of the parameters may be based on vectors of generated output signals and/or other (vectors of) determined parameters.

Metric module 111 of system 10 in FIG. 1 is configured to obtain sequences and/or sets of values of one or more metrics. The one or more metrics may quantify either one or more patient symptoms, one or more parameters related to lung function of subject 106, and/or any combination thereof. For example, the step of obtaining may include testing, measuring, and/or determining, e.g. based on output values generated by one or more sensors 142. In some embodiments, one metric may quantify one patient symptom or parameter. In some embodiments, one metric may quantify multiple patient symptoms or parameters. In some embodiments, multiple metrics may be aggregated and/or combined into one new metric, which may be simply referred to as a metric herein.

In some embodiments, sequences and/or sets of values may be measured.

Measurements may be obtained manually (e.g. performed by a human) or automatically (for example performed by machinery, e.g. under program control). Individual values in a sequence or set may correspond to different times. For example, an individual value may correspond to a measurement taken during a period spanning about 8 hours, about 12 hours, about 16 hours, about 20 hours, about 24 hours, about 2 days, about 3 days, and/or another suitable period. Multiple values may form a sequence by virtue of corresponding to subsequent, ordered, and/or overlapping periods. In some embodiments, individual values in a sequence and/or set may correspond to a time or period between about 8 hours and about 48 hours.

In some embodiments, metric module 111 may be configured to obtain a sequence of values of a first metric for subject 106 such that the first metric quantifies a patient symptom that is related to COPD. In some embodiments, the first metric quantifies multiple patient symptoms related to COPD. In some embodiments, the first metric quantifies lung function of subject 106. In some embodiments, the first metric quantifies multiple parameters related to lung function of subject 106. In some embodiments, the first metric quantifies a combination of one or more patient symptoms related to COPD with one or more parameters related to lung function of subject 106. For example, a metric obtained by metric module may be based on FEV1, sputum quantity sputum color, a cough metric, peak flow of subject 106, metrics related to spirometry, metrics commonly used for tele-health systems, and/or other metrics. Metric module 111 may be configured to obtain a sequence of values of one or metrics through a questionnaire that is provided by subject 106 and/or on behalf of subject 106. For example, the one or more metrics may include a score or count of the number of occurrences of an apnea during a sleep session. In some embodiments, the one or more metrics may include a score or count of various respiratory events, e.g. including Cheyne-Stokes respiration, central sleep apnea, obstructive sleep apnea, hypopnea, dyspnea, snoring, hyperventilation, and/or other respiratory events and/or combinations thereof. For example, one or more metrics may include and/or be based on an index of respiratory events (and/or other information), such as an apnea-hypopnea index (AHI), an obstructive apnea-hypopnea index, respiratory disturbance index (RDI), respiratory effort related arousal (RERA) index, obstructive respiratory disturbance index (ORDI), snore index, and/or any combination thereof. In some implementations, the obtained metrics as described herein may be aggregated and/or processed into a single score for a particular unit of time, e.g. between about 8 hours and about 48 hours.

The metrics and/or score described may be similar to information being tracked by (and/or on behalf of) subjects suffering from COPD. For example, such tracked information for COPD patients may be used to determine whether current levels of care need to be escalated to higher levels, up to and including hospitalization. For example, the metrics or score may be compared against a static and patient-specific baseline score.

The metrics, scores, and/or parameters used in a particular implementation may need to be oriented such that improvement and deterioration/exacerbation of the medical state of a subject is uniformly indicated by decreasing and increasing values, or vice versa, and not by a mixed indication. The description and illustrations herein assume that a lower value indicates improvement, but the disclosure is not intended to be limited in such a manner. For example, FEV1 may increase as lung function improves, whereas an index of respiratory events may decrease as the medical state of a subject improves. In other words, the orientation of these two metrics may be mixed (or non-uniform). For implementations in which such metrics are combined, one or more metrics may need to be adjusted and/or converted such that the orientations are uniform. For example, a metric may be inverted (from X to 1/X, or from X % to 100–X %) to accomplish proper orientation.

Figure 2:
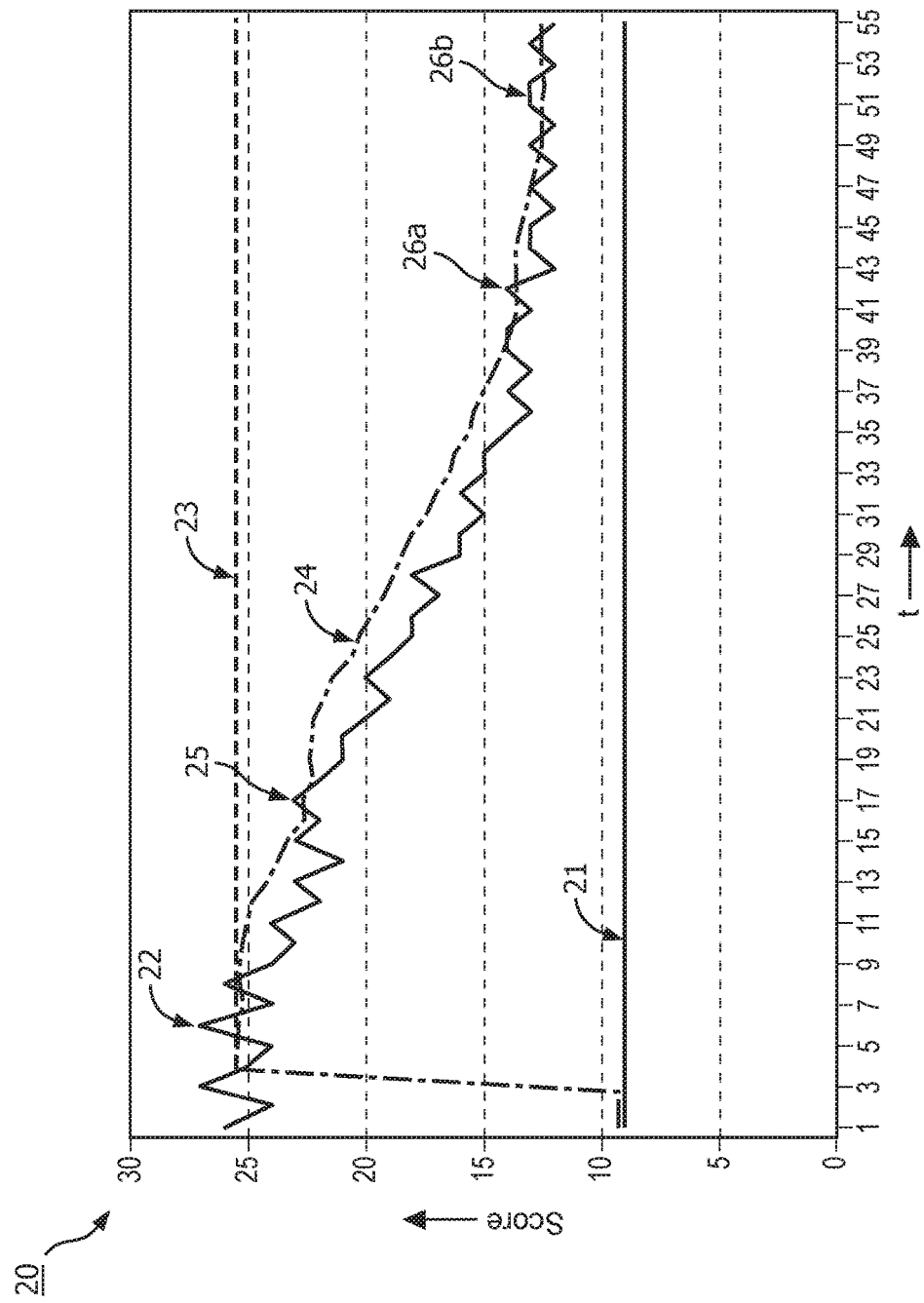
FIGS. 2-6 illustrate graphs depicting sequences of values of a metric that quantifies obtained measurements and/or symptoms over time.

By way of illustration, FIG. 2 illustrates graph 20 depicting a sequence of values of a particular metric for a particular subject, the sequence having been gathered over an extended period. The X-axis depicts time, e.g. measured in days. Assume that the origin of the X-axis corresponds to the moment the particular subject was discharged from the hospital. The Y-axis depicts a single score (per unit of time) based on one or more obtained metrics. Sequence 22 depicts values of the single score over time. Static baseline level 21 may depict the patient-specific pre-hospitalization baseline level, in this case having a value of approximately 9.

Most COPD patients need a period of about 20 days, about 30 days, about 45 days, about 60 days, about 90 days, about 120 days, and/or another period for their scores to stabilize after being discharged from the hospital. In some implementations, such a period may be referred to as Post Discharge Unstable Period, or PDUP. During the PDUP, post hospital-discharge COPD patients may need to be monitored and/or tracked separately from other, stable COPD patients. Ideally, the stabilized score for a post-hospital discharge patient may be at or near the pre-hospitalization baseline level, or even lower if the treatment (and/or patient-specific behavioral changes) turns out to be effective and/or successful. By way of non-limiting example, a patient-specific behavioral change may include a change in diet and/or exercise regime. More commonly, the stabilized score may be higher than the pre-hospitalization baseline level. Before a patient's score stabilizes, a comparison between such a score and the pre-hospitalization baseline level may not provide much helpful information pertaining to the need to alert and/or notify a caregiver. Based on such a comparison, a patient may be re-hospitalized prematurely, inadvertently, and/or unnecessarily. It may be undesirable, based on e.g. economic and other incentives, to re-admit patients to a hospital without a genuine need. In general, higher baseline levels, as determined over a period of one or more years, may indicate a medically relevant progression of a patient's COPD.

Referring to FIG. 1, dynamic baseline module 112 of system 10 in FIG. 1 is configured to determine dynamic baselines for subjects. Dynamic baseline module 112 may be configured to determine a first dynamic baseline for subject 106 by aggregating multiple individual values of a sequence of values of a metric obtained by metric module 111. For example, the first dynamic baseline may be based on 2, 3, 4, 6, 8, 10, 15, 20, 40, and/or another number of multiple individual values. In some embodiments, the first dynamic baseline may be based on between 4 and 10 individual values, between 10 and 20 individual values, between 4 and 20 individual values, and/or another range of individual values. In some embodiments, the first dynamic baseline may be based on a number of individual values that corresponds to a particular period, wherein the particular period may be about 8 hours, about 12 hours, about 16 hours, about 20 hours, about 1 day, about 36 hours, about 2 days, about 3 days, and/or another suitable period. In some implementations, the number of individual values used to determine the dynamic baseline may be inversely proportional to the duration of the period that corresponds to an individual value. For example, using 4 individual values that each correspond to a 24-hour period may be similar to using 16 individual values that each correspond to a 6-hour period, since each dynamic baseline covers and/or spans a 96-hour period.

In some implementations, the dynamic baseline at a particular moment $t_n$ may be based on immediately preceding values, up to moment $t_{n-1}$. In some implementations, the dynamic baseline at a particular moment $t_n$ may be based on older than immediately preceding values, e.g. up to moment $t_{n-2}$.

By way of illustration, in FIG. 2, sequence 24 depicts a dynamic baseline based on 4 values of sequence 22 (corresponding to 4 days). This number of values is exemplary and not intended to be limiting in any way. Sequence 24 may be referred to as dynamic baseline 24. As depicted in graph 20, sequence 24 defaults to static baseline level 21 for days 1-3, since not enough values of sequence 22 are available during days 1-3 to determine a proper 4-day average value. Other ways to aggregate multiple values are contemplated herein. For example, more recent values of sequence 22 may a larger effect or impact on the value of dynamic baseline 24 than older values, e.g. by weighing values differently. On day 4, the first non-trivial value for dynamic baseline 24 may be determined, in this case having a value of approximately 25. After the first few values are obtained for sequence 22, upper baseline 23 may be determined, for example by averaging the first 4 values of sequence 22. This number of values is exemplary and not intended to be limiting in any way. This number may not need to match the number of values used to determine dynamic baseline 24. In some implementations, a dynamic baseline may be based on a variable number of values, for example as many values as available, but, e.g., no more than a predefined maximum number. In such a case, the dynamic baseline may not need to default to static baseline level 21.

Referring to FIG. 1, alert module 113 of system 10 in FIG. 1 is configured to determine whether a caregiver needs to be notified regarding the medical state of a subject. For example, alert module 113 may be configured to determine whether the medical state of subject 106 is exacerbated such that a caregiver needs to be notified. Notification may include, e.g., a recommendation that a subject needs to be re-hospitalized. Determinations by alert module 113 may be based on a comparison of one or more individual values, as obtained by metric module 111, with a dynamic baseline, as determined by dynamic baseline module 112. In some implementations, the comparison may verify whether the difference between a current value for a metric and the value of the dynamic baseline exceeds a threshold. Such a comparison may be referred to as using a magnitude threshold. In some implementations, the comparison may verify whether the difference between a current value for a metric has exceeded the value of the dynamic baseline for at least a predetermined period, e.g. 2 or 3 days. Such a comparison may be referred to as using a duration threshold. Combinations of a magnitude threshold and a duration threshold are contemplated within the scope of this disclosure. Generally, thresholds may operate using a margin, such that a relatively small breach of a threshold may be deemed tolerable. In some implementations, determinations by alert module 113 may further be based on an upper baseline, such as upper baseline 23 in FIG. 2.

In some implementations, alert module 113 may be configured to determine whether the dynamic baseline has a positive slope in a particular period, e.g. the PDUP.

By way of illustration, in FIG. 2, the daily value of sequence 22 exceeds dynamic threshold 24 at value 25. Depending on the magnitude of this breach and the particular configuration for the determinations by the alert module, the system may determine at value 25 that a caregiver needs to be alerted and/or notified. Additional examples of a breach are labeled point 26a and point 26b.

Figure 3:
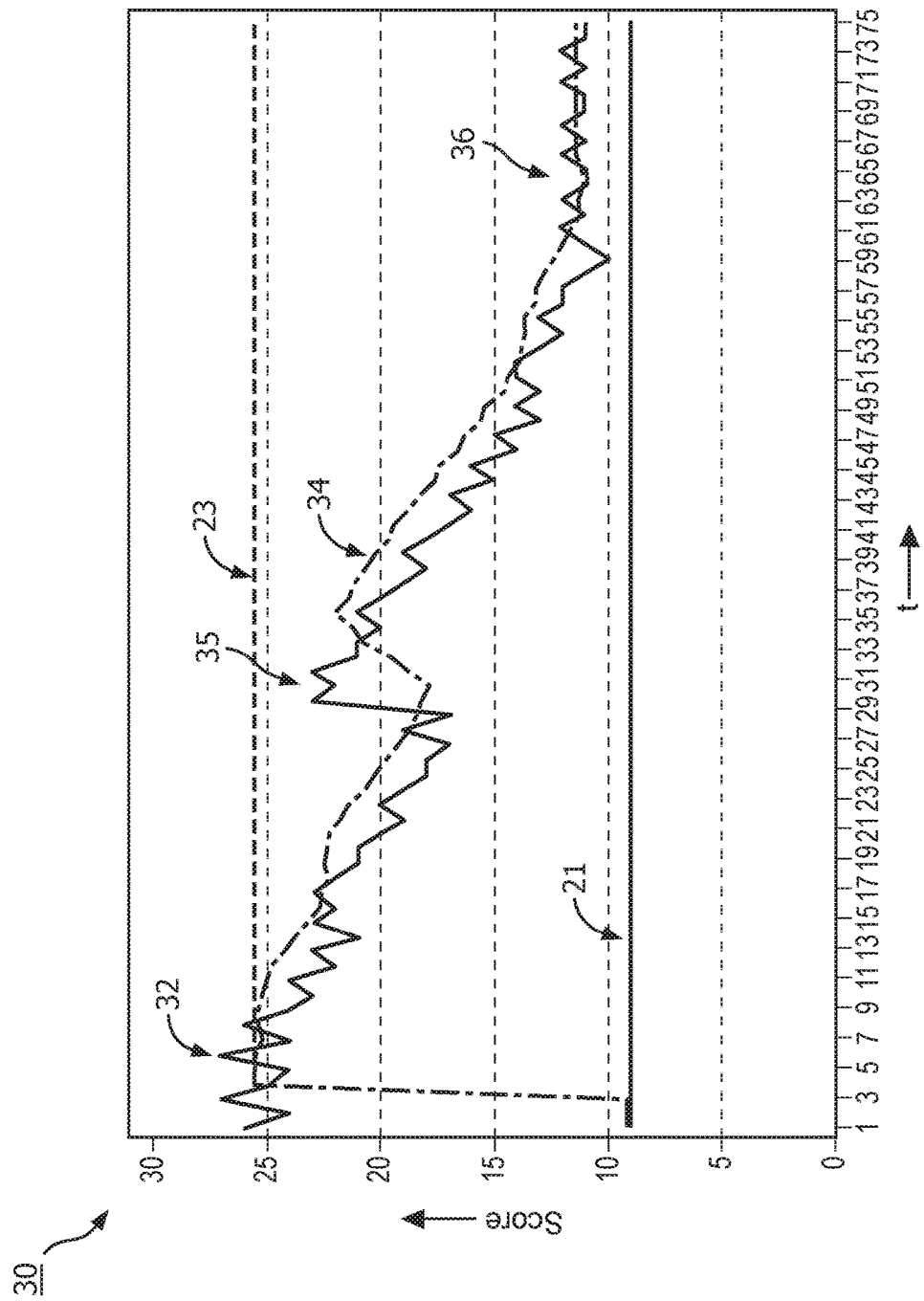

By way of illustration, FIG. 3 illustrates graph 30 depicting a sequence 32 of values of a particular metric for a particular subject, the sequence having been gathered over an extended period. Graph 30 spans about 75 days. Dynamic baseline 34 may be based on aggregating the preceding 4 or 5 individual values of sequence 32. The values of sequence 32 at or near moment 35 (e.g. approximately starting at day 29) exceed dynamic baseline 34 by a significant margin. The values of sequence 32 at or near moment 35 exceed dynamic baseline 34 during approximately 4 days. The slope of dynamic baseline 34 is reversed at or near moment 35, from a negative slope to a positive slope. The pattern depicted in graph 30 may indicate an exacerbation of the medical state of the particular subject, and may signify the need for medical intervention.

Referring to FIG. 1, dynamic baseline module 112 may be configured such that, responsive to an exacerbation of the medical state of subject 106, the determined dynamic baseline is held at a (temporarily) constant level. This constant level may be referred to as a temporarily "frozen" dynamic baseline. New (optional) values for the dynamic baseline may be determined, but, if (sufficiently) higher than the constant level, discarded in favor of the constant level. A newly determined (optional) value may actually be used as the dynamic baseline if this value fails the preceding test for being discarded. Alert module 113 may be configured to determine whether a caregiver needs to be notified regarding the medical state of subject 106 based on properties of the temporarily constant (dynamic) baseline. For example, alert module 113 may compare the duration during which the dynamic baseline is held constant (or "frozen") with a predetermined duration, and use such a comparison to make determinations as described elsewhere herein. For example, if subject 106 fails to recover within a week and bring a daily score below the temporarily constant (dynamic) baseline, a caregiver may need to be notified. Other ways to incorporate the constant level into determinations by alert module 113 are contemplated within the scope of this disclosure.

Figure 4:
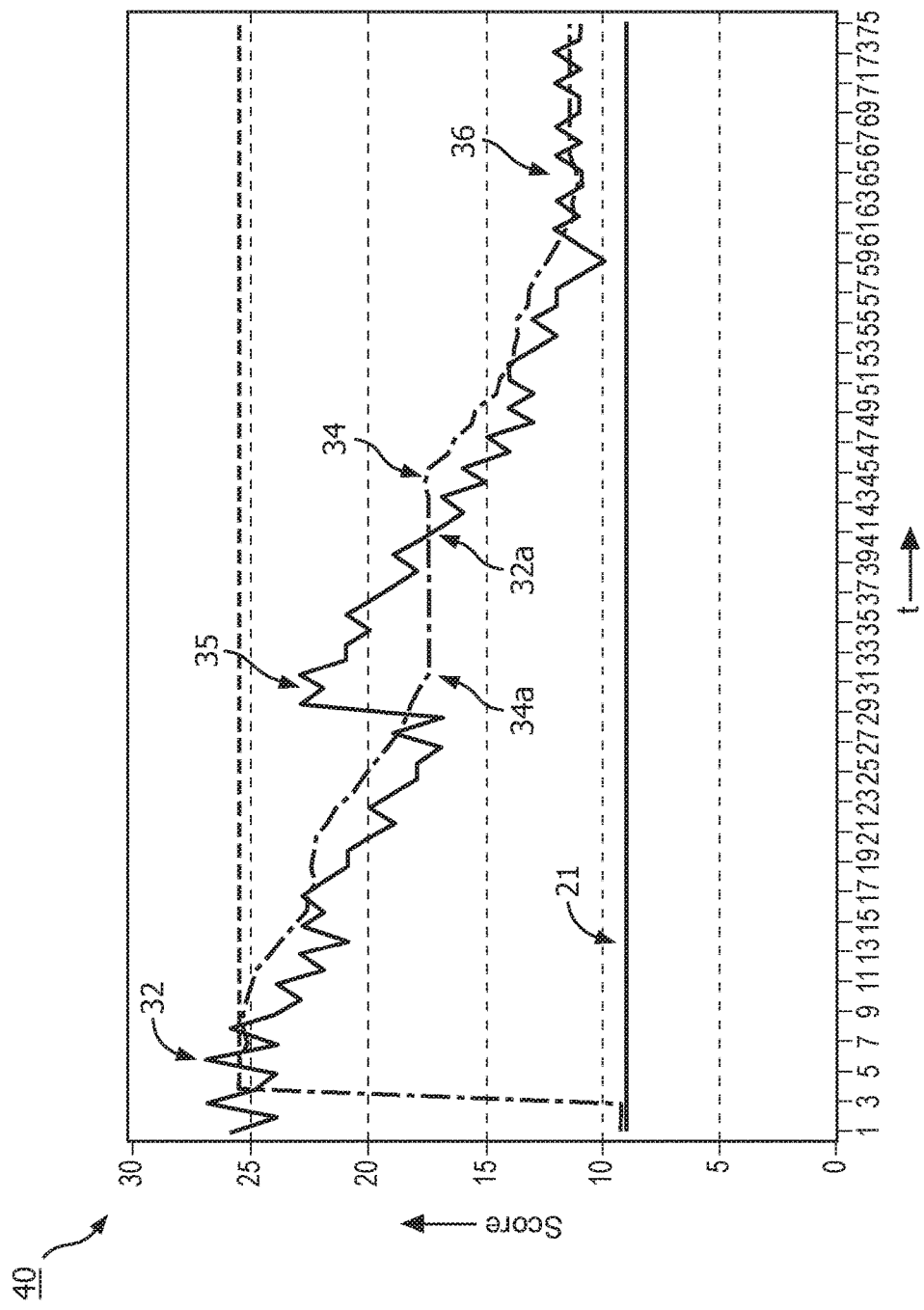

By way of illustration, FIG. 4 illustrates graph 40 depicting a sequence 32 of values of a particular metric for a particular subject, the sequence having been gathered over an extended period. Graph 40 spans about 75 days. Dynamic baseline 34 may be based on aggregating the preceding 4 or 5 individual values of sequence 32. The values of sequence 32 at or near moment 35 (e.g. approximately starting at day 29) exceed dynamic baseline 34 by a significant margin. The value of dynamic baseline 34 may be held constant starting at moment 34a (where it would have otherwise gone up based on the daily values of sequence 32). At daily value 32a the score is below the temporarily constant baseline. An alert module could use the duration from moment 34a to the moment corresponding to daily value 32a to make determinations about the need to notify a caregiver and/or the need for medical intervention. Alternatively, and/or simultaneously, an alert module could use the duration from moment 34a to the moment dynamic baseline 34 is no longer held constant (i.e. "unfrozen") to make determinations about the need to notify a caregiver and/or the need for medical intervention.

Figure 5:
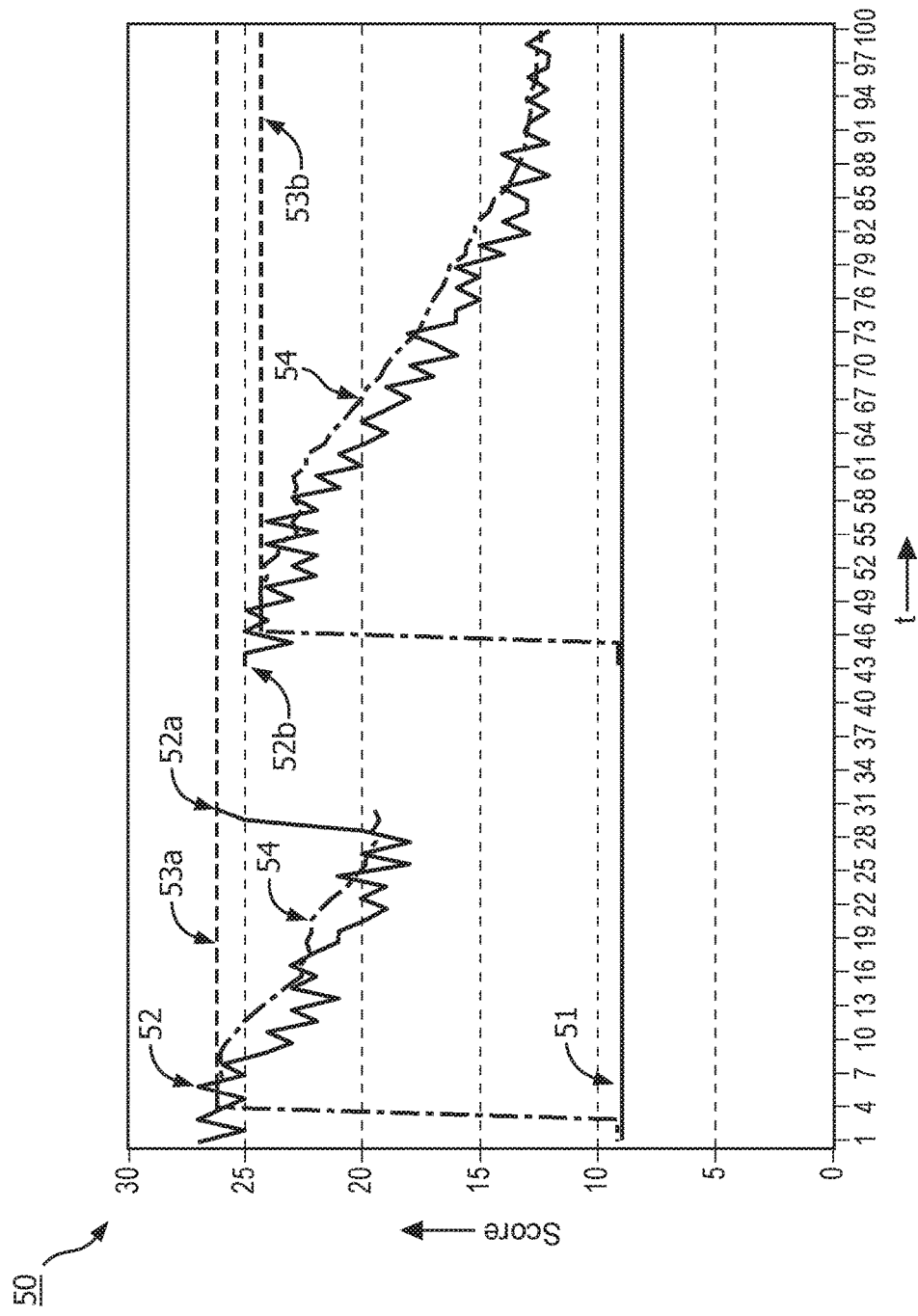

By way of illustration, FIG. 5 illustrates graph 50 depicting a sequence 52 of values of a particular metric for a particular subject, the sequence having been gathered over an extended period. Graph 50 spans about 100 days. Dynamic baseline 54 may be based on aggregating the preceding 4 or 5 individual values of sequence 52. Upper baseline 53a may be determined at or near day 4 of sequence 52, in this case at a value of approximately 26. Static baseline 51 may depict the patient-specific pre-hospitalization baseline level, in this case having a value of approximately 9. The values of sequence 52 at or near moment 52a (e.g. approximately starting at day 29) exceed dynamic baseline 54 by a significant margin, indicating an exacerbation of the medical state of the particular subject. In the example of FIG. 5, the exacerbation leads to re-hospitalization of the particular subject. Typically, the one or more metrics or score may be not tracked during a hospital stay, as depicted by the gap between sequence 52 at or near moment 52a and moment 52b. Moment 52b occurs approximately at day 44. A second upper baseline 53b may be determined at or near day 47 of sequence 52 (e.g. a few days after moment 52b), in this case at a value of approximately 24. In some implementations, neither the pre-hospitalization static baseline 51 nor the (first) upper baseline 53a are used in determining second upper baseline 53b. In some implementations, the entire described procedure for dynamic baselines and determinations by alert module 113 (as well as other described computer program modules) may be re-started from scratch upon re-hospitalization and/or other medical intervention that causes a gap in the obtained sequence of values of one or more metrics or a daily single score.

At some point during recovery, the medical state of subject 106 may (and likely will) stabilize, at least pertaining to COPD. At or around that point, the one or more metrics obtained by metric module 111 may stabilize. At some point after a patient's score stabilizes the use of a truly dynamic baseline may no longer be needed, and/or even be desirable. Instead, a newly determined static baseline may be used to monitor and/or track the patient. By way of illustration, in FIG. 2, the slope of dynamic baseline 24 may be flattening out at or around point 26a. By way of illustration, in FIGS. 3 and 4, the slope of dynamic baseline 34 may be flattening out at or around point 36.

Variability module 114 of system 10 in FIG. 1 is configured to determine a statistical measure, e.g. variability, for (multiple individual values of) one or more particular metrics. For example, variability may be based on one or more commonly used statistical measures, including but not limited to standard deviation, variance, interquartile range, coefficient of variation, and/or other measures of statistical dispersion. Variability may be determined for one or more metrics determined by metric module 111. In some implementations, variability may be determined for (daily) single scores, e.g. as depicted in FIGS. 2-5. If a metric or score stabilizes, the corresponding variability may be relatively low (compared to the variability during the PDUP). Once variability breaches a minimum threshold, i.e. goes below such a threshold (for a sufficiently long period), system 10 may be configured to automatically transition from using a dynamic baseline to using a newly determined static baseline. Once a static baseline is used instead of a dynamic baseline, determinations by alert module 113 may be based on a comparison between one or more individual values of a particular metric and the static baseline, with or without use of thresholds and/or margins. By way of illustration, in FIG. 2, the variability of dynamic baseline 24 may be breaching a minimum threshold at or around point 26a. By way of illustration, in FIGS. 3 and 4, the variability of dynamic baseline 34 may be breaching a minimum threshold at or around point 36.

Referring to FIG. 1, static baseline module 115 of system 10 in FIG. 1 is configured to determine static baselines for subjects. Static baselines may be determined by aggregating multiple individual values for a metric. Once determined, a static baseline may be held constant, e.g. until a medical intervention takes place, a caregiver takes action, and/or other reasons trigger the need to discard or update the baseline. The determination whether the moment to transition from using a dynamic baseline to a static baseline has occurred may be based on one or more determinations by variability module 114. Once system 10 uses a static baseline, determinations by alert module 113 may be based on the static baseline instead of a dynamic baseline. In some implementations, once system 10 uses a static baseline, a dynamic baseline may no longer be used or needed, at least until a medical intervention and/or re-hospitalization occurs.

In some implementations, system 10 may be configured to track multiple subjects in a manner similar to the manner described herein for subject 106. In some implementations, system 10 may be configured to track one or more subjects for a much longer term than the PDUP. For example, system 10 may be configured to track a subject for about 1 year, about 2 years, about 3 years, about 4 years, about 5 years, about 7 years, about 10 years, and/or another suitable period. Additional insight in one or more of the medical state of a particular subject, the progression of his COPD, the effects of different types and/or doses of medication, the effects of different types of therapies and/or medical devices used, the effects of changes to his treatment, patient-specific behavior, and/or patient-specific lifestyle, and/or other pertinent factors may be gleamed based on the information gathered and/or determined by system 10.

Long-term metric module 116 of system 10 is configured to compare progression of medical state over a period spanning at least a year. In some implementations, long-term metric module 116 may be configured to compare progression of medical state between multiple subjects. For example, a comparison between a first subject, a second subjects, and/or additional subjects may be made, spanning a period of at least a year. The comparison may include a series of static baselines for one or more subjects, information pertaining to re-hospitalizations of one or more subjects (e.g. number of occurrences, average duration, total days spent in a hospital, etc.), changes in patient stability over time, the rate of change for patient scores, and/or other pertinent long-term factors related to the medical state of COPD patients. Determinations by long-term metric module 116 may provide information about the efficiency and/or efficacy of certain types of therapy, treatment, and/or medication.

Figure 6:
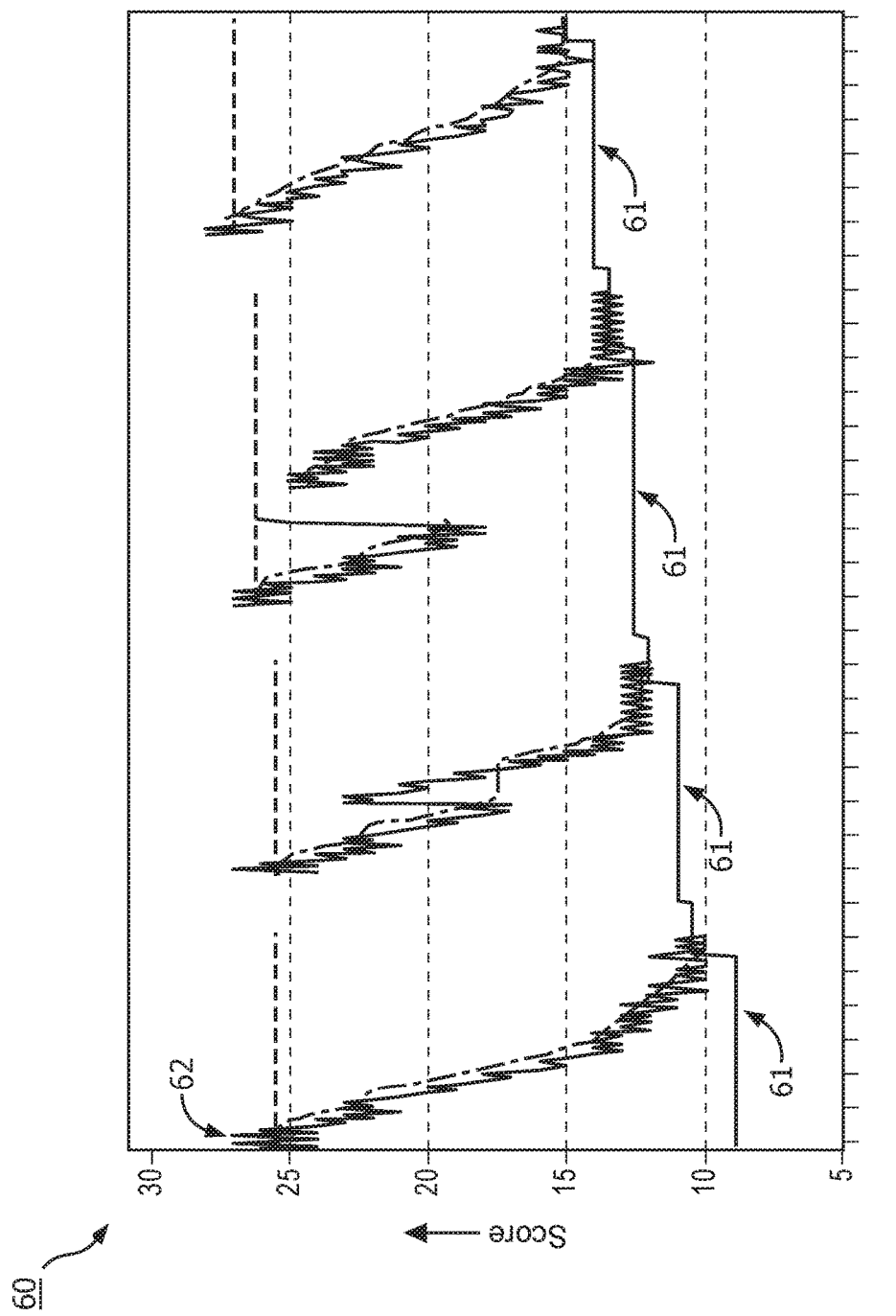

By way of illustration, FIG. 6 illustrates graph 60 depicting a sequence 62 of (daily) values of a particular metric for a particular subject, the sequence having been gathered over an extended period spanning more than one year. Gaps in sequence 62 indicate re-hospitalization. Graph 60 depicts the gradual rise of patient-specific static baseline 61 over time. Segments between hospitalizations may be similar to graphs depicted in FIGS. 2-5.

Figure 7:
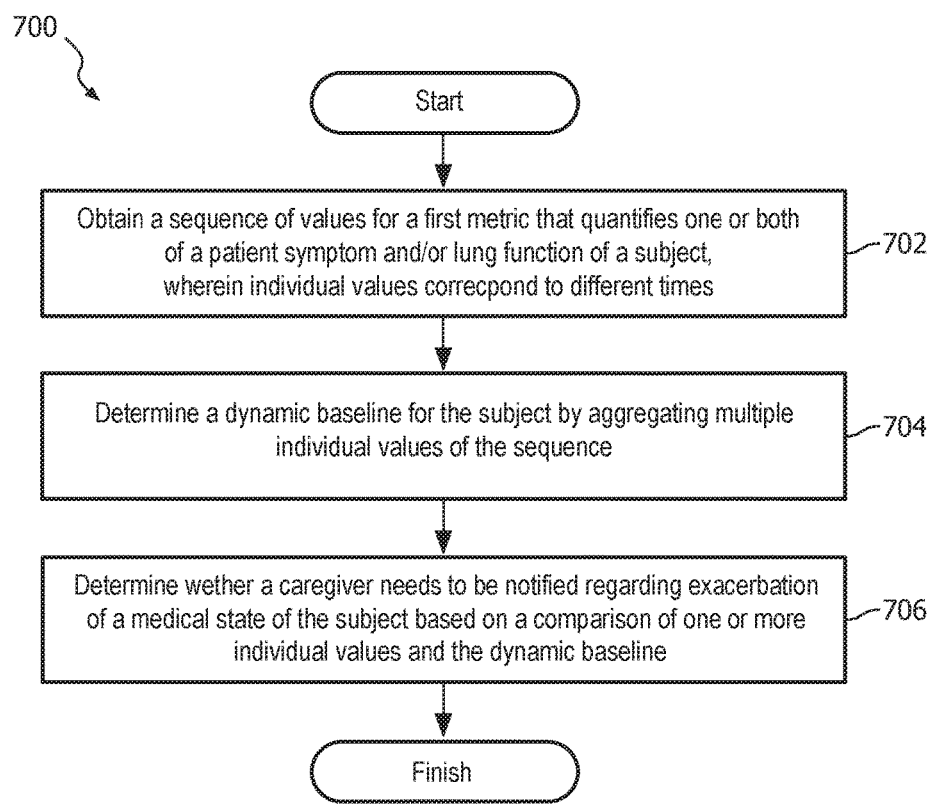
FIG. 7 illustrates a method to monitor subjects in accordance with one or more embodiments.

FIG. 7 illustrates a method 700 for monitoring subjects. The operations of method 700 presented below are intended to be illustrative. In certain embodiments, method 700 may be accomplished with one or more additional operations not described, and/or without one or more of the operations discussed. Additionally, the order in which the operations of method 700 are illustrated in FIG. 7 and described below is not intended to be limiting.

In certain embodiments, method 700 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, a sequence of values for a first metric that quantifies one or both of a patient symptom and/or lung function of a subject is obtained. The individual values correspond to different times, such that individual values in the sequence correspond to times during a period between 8 and 48 hours. In some embodiments, operation 702 is performed by a metric module the same as or similar to metric module 111 (shown in FIG. 1 and described herein).

At an operation 704, a first dynamic baseline is determined for the subject by aggregating multiple individual values of the sequence, the first dynamic baseline being based on between 4 and 20 individual values. In some embodiments, operation 704 is performed by a dynamic baseline module the same as or similar to dynamic baseline module 111 (shown in FIG. 1 and described herein).

At an operation 706, whether a caregiver needs to be notified regarding exacerbation of a medical state of the subject is determined. The determination is based on a comparison of one or more individual values for the first metric from the sequence and the first dynamic baseline. In some embodiments, operation 706 is performed by an alert module the same as or similar to alert module 113 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although this description includes details for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that, to the extent possible, one or more features of any embodiment are contemplated to be combined with one or more features of any other embodiment.

The invention claimed is:

1. A system configured to detect exacerbations based on dynamically-updated threshold values, the system comprising:

one or more hardware processors configured by machine readable instructions to:
obtain a sequence of values for a metric that quantifies a lung-related characteristic of a subject, each value of the sequence corresponding to a time during a defined period different from a time to which at least another value of the sequence corresponds;
determine, based on a set of values of the sequence, a dynamic threshold for the subject;
adjust the dynamic threshold for the subject multiple times during the defined period based on other sets of values of the sequence, wherein each of the other sets of values includes at least one particular value that is not included in another set of values of the sequence, wherein a quantity of values in an individual set is inversely proportional to a duration of time that corresponds to the individual set;
compare one or more values of the metric to the multiple-adjusted dynamic threshold;
responsive to the comparison indicating exacerbation of a medical state of the subject, temporarily hold a current level of the multiple-adjusted dynamic threshold constant for a period of time; and
provide a notification to a caregiver based on a comparison of one or more additional values of the metric with the temporarily held current level of the multiple-adjusted dynamic threshold, wherein the notification indicates an ongoing exacerbation of the medical state of the subject.

2. The system of claim 1, wherein the defined period is between 8 hours and 48 hours.

3. The system of claim 1, wherein the one or more hardware processors are further configured such that providing the notification to the caregiver is based on whether a difference between one or more individual values of the additional values for the metric and the temporarily held current level of the multiple-adjusted dynamic threshold breaches a duration threshold.

4. The system of claim 1, wherein the one or more hardware processors are further configured to:
determine variability of multiple individual values for the metric, such that a variability is determined of multiple individual values for the metric; and
determine static thresholds for subjects, such that a static threshold is determined for the subject by aggregating multiple individual values for the metric, wherein determination of the static threshold is based on the variability,
wherein providing the notification to the caregiver is based on a comparison of one or more individual values of the metric and the static threshold.

5. The system of claim 1, further comprising one or more sensors configured to generate output signals conveying information related to one or more parameters associated with one or both of a patient symptom related to chronic obstructive pulmonary disease (COPD) and/or lung function of the subject, wherein the sequence of values for the metric is obtained based on the output signals generated by the one or more sensors.

6. The system of claim 1, wherein the one or more hardware processors are further configured to obtain a second sequence of values for a second subject, determine a second multiple-adjusted dynamic threshold for the second subject, determine whether the caregiver needs to be notified regarding exacerbation of a medical state of the second subject, and compare progression of medical states between the subject and the second subject spanning a period of at least a year, wherein the comparison is based on determinations of whether the caregiver needed to be notified regarding exacerbation of the medical state of the subject and the second subject during the year.

7. The system of claim 1, wherein the one or more hardware processors are configured to temporarily hold the current level of the multiple-adjusted dynamic threshold constant until one or more of the one or more additional values of the metric breach the temporarily held constant current level of the multiple-adjusted dynamic threshold.

8. A method for detecting exacerbations based on dynamically-updated threshold values with an exacerbation detection system, the system comprising one or more hardware processors configured by machine readable instructions, the method comprising:
obtaining, with the one or more hardware processors, a sequence of values for a metric that quantifies a lung-related characteristic of a subject, each value of the sequence corresponding to a time during a defined period different from a time to which at least another value of the sequence corresponds;
determining, with the one or more hardware processors, based on a set of values of the sequence, a dynamic threshold for the subject;
adjusting, with the one or more hardware processors, the dynamic threshold for the subject multiple times during the defined period based on other sets of values of the sequence, wherein each of the other sets of values includes at least one particular value that is not included in another set of values of the sequence, wherein a quantity of values in an individual set is inversely proportional to a duration of time that corresponds to the individual set;
comparing, with the one or more hardware processors, one or more values of the metric to the multiple-adjusted dynamic threshold;
responsive to the comparison indicating exacerbation of a medical state of the subject, temporarily holding, with the one or more hardware processors, a current level of the multiple-adjusted dynamic threshold constant for a period of time; and
providing, with the one or more hardware processors, a notification to a caregiver based on a comparison of one or more additional values of the metric with the temporarily held current level of the multiple-adjusted dynamic threshold, wherein the notification indicates an ongoing exacerbation of the medical state of the subject.

9. The method of claim 8, wherein the defined period is between 8 hours and 48 hours.

10. The method of claim 8, wherein providing the notification to the caregiver is based on whether a difference between one or more individual values of the additional values for the metric and the temporarily held current level of the multiple-adjusted dynamic threshold breaches a duration threshold.

11. The method of claim 8, further comprising:
determining, with the one or more hardware processors, a variability of multiple individual values for the first metric; and
determining, with the one or more hardware processors, a static threshold for the subject by aggregating multiple individual values for the metric, wherein determination of the static threshold is based on the variability, wherein providing the notification to the caregiver is based on a comparison of one or more individual values of the metric and the static threshold.

12. The method of claim 8, wherein the system further comprises one or more sensors configured to generate output signals conveying information related to one or more parameters associated with one or both of a patient symptom related to chronic obstructive pulmonary disease (COPD) and/or lung function of the subject, the method further comprising:
generating, with the one or more sensors, the output signals conveying information related to one or more parameters associated with one or both of the patient symptom related to COPD and/or lung function of the subject, wherein the sequence of values for the metric is obtained based on the output signals.

13. The method of claim 8, further comprising:
obtaining, with the one or more hardware processors, a second sequence of values for the metric that quantifies one or both of a patient symptom and/or lung function of a second subject, wherein individual values in the second sequence correspond to different times, such that individual values in the second sequence correspond to times during a period between 8 and 48 hours;
determining, with the one or more hardware processors, a second multiple-adjusted dynamic threshold for the second subject by aggregating multiple individual values of the second sequence, the second multiple-adjusted dynamic threshold being based on between 4 and 20 individual values;
determining, with the one or more hardware processors, whether the caregiver needs to be notified regarding exacerbation of a medical state of the second subject, wherein the determination is based on a comparison of one or more individual values for the metric from the second subject and a second multiple-adjusted dynamic threshold that is constant for a second period of time; and
comparing, with the one or more hardware processors, progression of medical states between the subject and the second subject spanning a period of at least a year, wherein the comparison is based on determinations of whether the caregiver needed to be notified regarding exacerbation of the medical states of the subject and the second subject.

14. The method of claim 8, wherein the one or more hardware processors are configured to temporarily hold the current level of the multiple-adjusted dynamic threshold constant until one or more of the one or more additional values of the metric breach the temporarily held constant current level of the multiple-adjusted dynamic threshold.

15. A system configured to detect exacerbations based on dynamically-updated threshold values, the system comprising:
means for obtaining a sequence of values for a metric that quantifies a lung-related characteristic of a subject, each value of the sequence corresponding to a time during a defined period different from a time to which at least another value of the sequence corresponds;
means for determining, based on a set of values of the sequence, a dynamic threshold for the subject;
means for adjusting the dynamic threshold for the subject multiple times during the defined period based on other sets of values of the sequence, wherein each of the other sets of values includes at least one particular value that is not included in another set of values of the sequence, wherein a quantity of values in an individual set is inversely proportional to a duration of time that corresponds to the individual set;
means for comparing one or more values of the metric to the multiple-adjusted dynamic threshold;
responsive to the comparison indicating exacerbation of a medical state of the subject, means for temporarily holding a current level of the multiple-adjusted dynamic threshold constant for a period of time; and
means for providing a notification to a caregiver based on a comparison of one or more additional values of the metric with the temporarily held current level of the multiple-adjusted dynamic threshold, wherein the notification indicates an ongoing exacerbation of the medical state of the subject.

16. The system of claim 15, wherein the defined period is between 8 hours and 48 hours.

17. The system of claim 15, wherein operation of the means for providing a notification to the caregiver is based on whether a difference between one or more values of the additional values of the metric and the temporarily held current level of the multiple-adjusted dynamic threshold breaches a duration threshold.

18. The system of claim 15, further comprising:
means for determining a variability of multiple individual values of the metric; and
means for determining a static threshold for the subject by aggregating multiple individual values of the metric, wherein determination of the static threshold is based on the variability, wherein operation of the means for providing a notification to the caregiver is based on a comparison of one or more individual values of the metric and the static threshold.

19. The system of claim 15, further comprising:
means for generating output signals conveying information related to one or more parameters associated with one or both of a patient symptom related to chronic obstructive pulmonary disease (COPD) and/or lung function of the subject, wherein operation of the means for obtaining the sequence of values for the first metric is based on the output signals.

20. The system of claim 15, wherein the means for obtaining the sequence is further configured to obtain a second sequence of values for the metric that quantifies one or both of a patient symptom and/or lung function of a second subject, wherein individual values correspond to different times, such that individual values in the second sequence correspond to times during a period between 8 and 48 hours,
wherein the means for determining the dynamic threshold is further configured to determine a second multiple-adjusted dynamic threshold for the second subject by aggregating multiple individual values of the second sequence, the second multiple-adjusted dynamic threshold being based on between 4 and 20 individual values,
wherein the means for providing the notification to the caregiver is further configured to determine whether the caregiver needs to be notified regarding exacerbation of a medical state of the second subject, wherein the determination is based on a comparison of one or more individual values of the metric from the second subject and a second multiple-adjusted dynamic threshold that is held constant for a second period of time, the system further comprising:
means for comparing progression of medical states between the subject and the second subject spanning a period of at least a year, wherein the comparison is based on determinations of whether the caregiver needed to be notified regarding exacerbation of the medical state of the subject or the second subject during the year.

* * * * *